US008765387B2

(12) United States Patent
Ambrus et al.

(10) Patent No.: US 8,765,387 B2
(45) Date of Patent: Jul. 1, 2014

(54) METHOD OF DIAGNOSING SJOGREN'S DISEASE

(75) Inventors: Julian L. Ambrus, Buffalo, NY (US); Long Shen, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 38 days.

(21) Appl. No.: 13/574,265

(22) PCT Filed: Jan. 21, 2011

(86) PCT No.: PCT/US2011/021992
§ 371 (c)(1),
(2), (4) Date: Oct. 26, 2012

(87) PCT Pub. No.: WO2011/091220
PCT Pub. Date: Jul. 28, 2011

(65) Prior Publication Data
US 2013/0040322 A1 Feb. 14, 2013

Related U.S. Application Data

(60) Provisional application No. 61/297,167, filed on Jan. 21, 2010.

(51) Int. Cl.
*G01N 33/53* (2006.01)
(52) U.S. Cl.
USPC .............................................. 435/7.1; 435/7.2
(58) Field of Classification Search
None
See application file for complete search history.

(56) References Cited

U.S. PATENT DOCUMENTS

| 5,895,812 A | 4/1999 | Laurie et al. |
| 2007/0184502 A1 | 8/2007 | Matthias et al. |
| 2007/0184511 A1 | 8/2007 | Dawson et al. |
| 2012/0058933 A1* | 3/2012 | Gorr .............................. 514/1.4 |

FOREIGN PATENT DOCUMENTS

WO 9841649 A2 9/1998

OTHER PUBLICATIONS

Ruan, Q., et al., The Autoimmune Regulator Directly Controls the Expression of Genes Critical for Thymic Epithelial Function, J. Immunol., 2007, vol. 178, pp. 7173-7180.
Hu, S., et al., Salivary Proteomic and Genomic Biomarkers for Primary Sjogren's Syndrome, Arthritis & Rheumatism, Nov. 2007, vol. 56, No. 11, pp. 3588-3600.
Shen, L. et al. Novel autoantibodies in Sjogren's syndrome, Clinical Immunology, Oct. 12, 2012, vol. 145, pp. 251-255.
Bayetto, K. et al. Sjogren's syndrome: a review of aetiology, pathogenesis, diagnosis and management, Australian Dental Journal, Jun. 1, 2010, vol. 55, pp. 39-47.

* cited by examiner

*Primary Examiner* — Jacob Cheu
(74) *Attorney, Agent, or Firm* — Hodgson Russ LLP

(57) ABSTRACT

Provided are methods and compositions for determining whether an individual has Sjögren's disease (SD). The method entails determining in a biological sample from the individual the presence of antibodies directed to salivary gland protein 1 (SP-I), parotid secretory protein (PSP), carbonic anhydrase 6 (C A6), or determining a combination of the antibodies. Determining that the individual has SD is based on the presence of the antibodies. The method provides for detection of early SD. Kits for antibody detection containing the antigens to which the antibodies of SD patients are directed are also provided.

9 Claims, 2 Drawing Sheets

| | Marker | CA6 | PSP | SP-1 |
|---|---|---|---|---|
| Patient with Sjogren's Disease | | ↓ | ↓ | ↓ |
| Normal Control | | ↓ | ↓ | ↓ |

//
METHOD OF DIAGNOSING SJOGREN'S DISEASE

This application claims priority to U.S. provisional application No. 61/297,167, filed Jan. 21, 2010, the disclosure of which is incorporated herein by reference.

BACKGROUND OF THE INVENTION

Sjogren's disease is a common autoimmune disorder with significant morbidity and mortality secondary to destruction of the salivary and lachrymal glands. It involves both local and systemic autoimmunity and is generally recognized only after salivary and lachrymal glands are destroyed resulting in dry mouth and dry eyes (Borchers, A. T., S. M. Naguwa, C. L. Keen, and M. E. Gershwin. 2003. Immunopathogenesis of Sjogren's syndrome. Clin Rev Allergy Immunol 25:89-104; Delaleu, N., R. Jonsson, and M. M. Koller. 2005. Sjogren's syndrome. Eur J Oral Sci 113:101-113). Sjögren's syndrome is a common syndrome affecting 0.5% of the population with a strong female predominance (Delaleu, N., R. Jonsson, and M. M. Koller. 2005. Sjögren's syndrome. Eur J Oral Sci 113:101-113, Fox, R. I. 2005. Sjogren's syndrome. *Lancet* 366:321-331.). It consists of xerostomia and xerophthalmia and may be due to several causes including aging, infections, medications, environmental toxins and autoimmune responses (Daniels, T. E. 2000. Evaluation, differential diagnosis, and treatment of xerostomia. *J Rheumatol Suppl* 61:6-10). Sjögren's disease is a primary disorder consisting of Sjogren's syndrome with systemic manifestations including lymphadenopathy, interstitial pneumonitis and mild renal disease (Borchers, A. T., S. M. Naguwa, C. L. Keen, and M. E. Gershwin. 2003. Immunopathogenesis of Sjögren's syndrome. Clin Rev Allergy Immunol 25:89-104; Delaleu, N., R. Jonsson, and M. M. Koller. 2005. Sjogren's syndrome. Eur J Oral Sci 113:101-113). Sjögren's syndrome is often seen in association with other autoimmune diseases, especially systemic lupus erythematosus (SLE) (Manoussakis, M. N., et al. Moutsopoulos. 2004. Sjogren's syndrome associated with systemic lupus erythematosus: clinical and laboratory profiles and comparison with primary Sjogren's syndrome. *Arthritis Rheum* 50:882-891). Patients with Sjögren's disease often have hypergammaglobulinemia, and various autoantibodies, especially to Ro and La (Fox, R. I. 2005. Sjogren's syndrome. *Lancet* 366:321-331, Lazarus, M. N., and D. A. Isenberg. 2005. Development of additional autoimmune diseases in a population of patients with primary Sjogren's syndrome. *Ann Rheum Dis* 64:1062-1064, ansen, A., P. E. Lipsky, and T. Dorner. 2005. Immunopathogenesis of primary Sjögren's syndrome: implications for disease management and therapy. *Curr Opin Rheumatol* 17:558-565). Almost 4% of patients with Sjögren's disease will develop lymphoma, predominantly B cell non-Hodgkin lymphomas.

The diagnosis of Sjogren's disease is generally made when dry eyes causes irritation and corneal abrasions, and dry mouth causes difficulty swallowing and dental caries. Biochemical diagnosis is based on detection of lymphocytes infiltrating the salivary glands and serum auto antibodies directed towards Ro and La. Current therapies involve the use of artificial tears and saliva as well as cholinergic drugs to enhance secretions from the few remaining glandular cells (the disclosure of the following three citations are incorporated herein by reference: Kassan, S. S., and H. M. Moutsopoulos. 2004. Clinical manifestations and early diagnosis of Sjogren syndrome. Arch Intern Med 164:1275-1284, Latkany, R. 2008. Dry eyes: etiology and management. Current Opinion in Ophthalmology 19:287-291, Thanou-Stavraki, A., and J. A. James. 2008. Primary Sjogren's syndrome: Current and prospective therapies. Seminars in Arthritis and Rheumatism 37:273-292). However, no current therapies restore salivary and lachrymal gland function because the glands are largely destroyed by the time the disease is identified. It would therefore be of great benefit to be able to diagnose Sjogren's disease early since that is when it is amenable for treatment, but no such diagnostic methods exist. Thus, there is an ongoing and unmet need for improved methods for diagnosing Sjogren's disease, and in particular for use in diagnosis before the diseases progresses to a point where current therapeutic approaches are inadequate.

SUMMARY OF THE INVENTION

The present invention provides a method for determining whether an individual has Sjögren's disease (SD). The method comprises determining in a biological sample from the individual the presence of antibodies directed to salivary gland protein 1 (SP-1), parotid secretory protein (PSP), carbonic anhydrase 6 (CA6), or determining a combination of the antibodies. Determining that the individual has SD is based on the presence of the antibodies. Also provided is a method for determining that an individual does not have SD which comprises determining in a biological sample obtained from the individual the absence of detection of antibodies to PSP, and SP-1 and determining based on the absence of detection of the antibodies that the individual does not have SD. The individual may also have less antibodies to CA6 relative to an SD patient. Any PSP or CA6 protein may be used. However, there is no known human homologue to SP-1, and the invention accordingly provides a novel and unexpected discovery that humans with SD produce autoantibodies that recognize non-human SP-1, and in particular murine SP-1. It is expected that SP-1 produced in other non-human mammals can also be used for detecting anti-SP-1 antibodies.

The method of the invention can be used to diagnose SD in any individual of any age or gender, and at any stage of the disease. In one embodiment, the invention is used to detect early SD.

The antibodies that are positively associated with SD and described further herein can be detected using any suitable method and/or reagents for detecting antibodies. In one embodiment, the antibodies are detected using an ELISA assay.

The invention also provides kits comprising the antigens to which the antibodies of SD patients are directed and may further comprise components for biological sample collection, reagents for antibody detection, control reaction, and other materials useful for detecting antibodies. In one embodiment, the invention provides a kit comprising purified SP-1, PSP and CA6 proteins or fragments thereof that are recognized by antibodies produced by SD patients. The proteins may be provided in isolated and purified form, and they may be covalently or non-covalently associated with a solid matrix.

DESCRIPTION OF THE INVENTION

Figure 1:
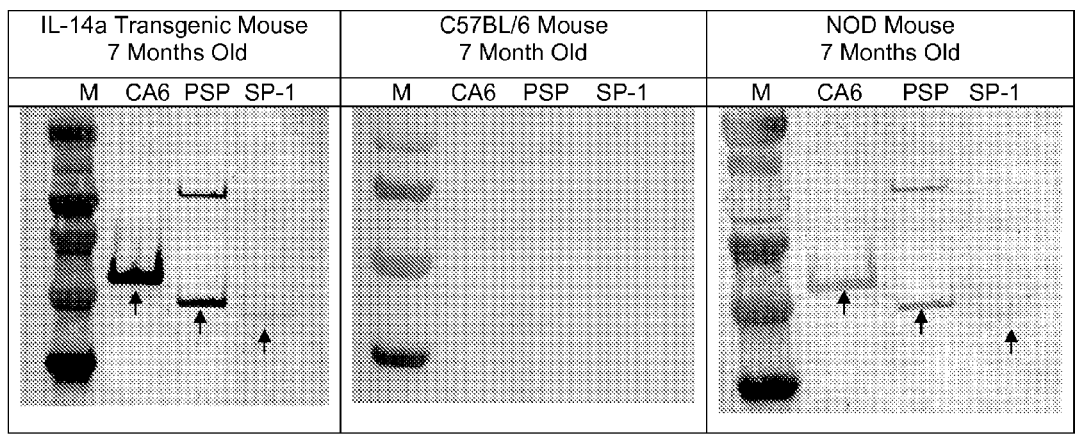
FIG. 1 provides a photographic representation of Western blotting for autoantibodies in the sera of IL-14aTG mice during early stages of Sjogren's Disease. To obtain the data summarized in FIG. 1, sera were collected from IL-14αTG mice, NOD and C57BL/6 mice at 7 months of age. Custom expressed and purified salivary gland protein 1 (SP-1), parotid secretory protein (PSP) and carbonic anhydrase 6 (CA6) were used to run Western blots with these sera. Data shown are representative of 6 mice studied in each group. The left panel shows the serum of an IL-14αTG mouse that recognizes CA6 and PSP strongly and SP-1 weakly. The middle panel shows the same study with the serum of a C57BL/6 mouse. C57BL/6 sera bound none of these auto-antigens. The right panel shows the same study with the serum of an NOD mouse. Both CA6 and PSP are strongly recognized by this serum.

The present invention provides a method for determining whether an individual has Sjögren's disease (SD). The method comprises determining in a biological sample obtained from the individual the presence of antibodies to salivary gland protein 1 (SP-1), parotid secretory protein (PSP), carbonic anhydrase 6 (CA6), or a combination of the SP-1, PSP and CA6 antibodies. The individual is identified as having SD if such antibodies or combinations thereof are present.

The invention provides the first identification of a positive correlation between SD and antibodies to any of SP-1, PSP and CA6. Our discovery that human SD patients produce antibodies that recognize murine SP-1 was particularly unexpected because there is no known human homologue to this protein. Thus, the invention provides a surprising and novel method for identifying individuals who have SD. The invention further provides for identifying an individual as not having SD if antibodies to SP-1 and PSP are not detected in a biological sample obtained from the individual.

In addition to antibodies to SP-1, PSP and CA6, antibodies to other markers can be determined in the method of the invention for evaluating whether or not an individual has SD. Non-limiting examples of such antibodies include those directed to lymphotoxin (LTA), mucin 10 (submandibular gland salivary mucin), salivary amylase 1, Ro, La, muscarinic receptor 3, fodrin, and the cytokines IL-14 and interferon-α.

Our demonstration that production of antibodies to SP-1, PSP and CA6 are indicative of SD is supplemented by research we performed on clinically relevant animal models of SD. In this regard, we have developed an animal model that reproduces all the immunological and clinical features seen in patients with SD in the same relative time frame. The animal model we developed is referred to as the IL-14alpha transgenic mouse (IL14aTG). Using this model we have demonstrated that lymphocytic infiltration of the salivary glands occurs after the glands have already been destroyed and that only a small percentage of the mice develop antibodies to Ro and La. Our data also demonstrate that LTA is important to early salivary gland injury in IL14aTG and the NOD mouse models of SD, and that IL-14aTG mice lacking LTA (IL-14aTG.LTA−/−) retain normal salivary gland function and suffer no lymphocytic infiltration of their salivary glands. We also demonstrate that LTA is found in the serum of human SD patients.

IL-14aTG mice, like patients with SD, produce interferon-α (IFN-a) systemically and lymphotoxin (LTA) locally in the salivary glands. Autoantibodies are deposited in the salivary gland at the time that salivary gland function is lost. The auto-antigens recognized at this stage are different than the auto-antigens seen later in the disease, Ro and La, which traditionally have been felt to be characteristic of SD. We have also demonstrated in this model that salivary gland function is lost before infiltration of the salivary glands with lymphocytes. In summary, and without intending to be bound by any particular theory, it is considered that IL-14aTG mice reproduce all the features of SD seen in patients in the same relative time frame. Further, SD occurs in all IL-14aTG mice tested. The time course of SD in IL-14aTG mice is 1) hypergammaglobulinemia and early antibody production at 6 months of age, 2) decreased salivary gland function with lymphocytic infiltration of only the submandibular glands, but antibody deposition in the submandibular and parotid glands at 10 months, 3) lymphocytic infiltration of the submandibular, parotid and lachrymal glands with B and T cells and plasma cells along with mild renal and lung disease at 14 months, and 4) large B cell lymphoma at 18 months. Note that loss of salivary gland function occurs several months before lymphocytic infiltration of the salivary glands, which indicates there is antibody and/or cytokine mediated injury that occurs before lymphocytic infiltration of the glands. Furthermore, as noted above, the IL-14aTG mice generally do not produce anti-Ro and anti-La antibodies during the early stages of the disease. The pattern of immunofluorescence for immunoglobulin deposition in the salivary glands varies over time, suggesting that different auto antigens are likely to be important at various stages of the disease. Additionally, IL-14aTG mice do not develop diabetes, like NOD mice, or proliferative glomerulonephritis, like (NZBxNZW) F1 and MRL/1pr mice. The IL-14aTG mouse is thus the only animal model of SD that develops all the features of Sjogren's disease in the absence of other autoimmune diseases. Accordingly, the IL-14aTG and IL-14aTG.LTA mice are valuable for identifying early events in the development of SD.

Figure 2:
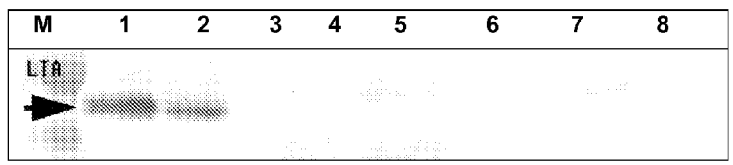
FIG. 2 provides a photographic representation of Western blotting results demonstrating that lymphotoxin is found in the salivary gland secretions of IL-14a TG mice but not littermate controls.
Figure 3:
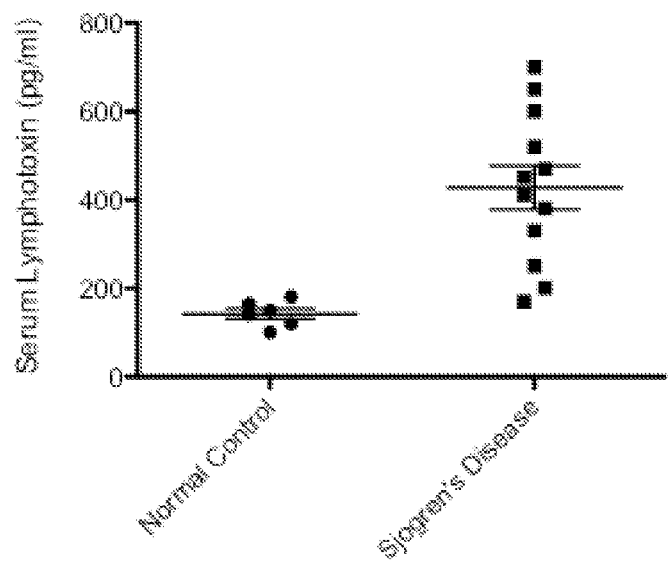
FIG. 3 provides a graphical representation of data showing that lymphotoxin is found in the sera of selected patients with Sjogren's disease.
Figures 4, 5:
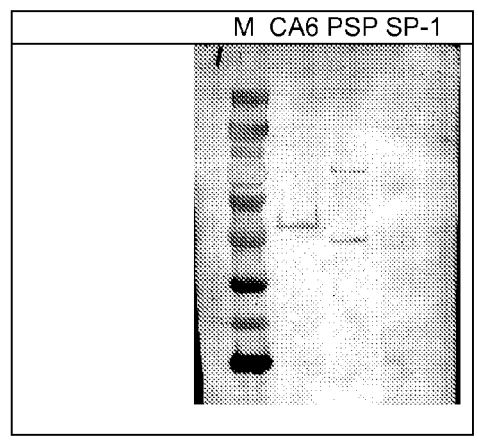
FIG. 4 provides a photographic representation of Western blotting showing autoantibodies in the sera and salivary glands of IL-14aTG.LTA−/− mice. The data show that the serum of an IL-14aTG.LTA−/− mouse at 11 months of age reacts with CA6 and PSP.
FIG. 5 provides a photographic representation of Western blotting results showing that sera from Patients with Sjogren's Disease Contain Autoantibodies to CA6, PSP and SP-1. The Western blots were performed as in FIG. 1 except sera were used from patients with Sjogren's disease or aged matched normal controls. Five patients and two normal controls were evaluated. Data shown are from one representative patient (all five patients showed similar results) and one normal control (both normal controls showed similar results). Patients with SD but not normal controls have antibodies to PSP and SP-1.

We identified the SD antigens disclosed herein in part by examining the expression of mRNA in the spleens of IL14aTG mice. We have produced purified antigens encoded by these mRNAs and have shown that IL14aTG and NOD mouse models of SD develop antibodies to these antigens during the early course of their disease (FIG. 1). We have also demonstrated that lymphotoxin is present in the salivary gland secretions of IL14aTG mice during the early course of their disease, and that elimination of lymphotoxin prevents the development of salivary gland injury (FIG. 2). We have shown that lymphotoxin is present in the sera of human patients with SD (FIG. 3). Further, we have demonstrated the presence of antibodies to SD antigens in IL-14aTG.LTA−/− mice (FIG. 4.) Further still, we also demonstrate that sera from human patients with SD contain autoantibodies to CA6, PSP and SP-1 (the latter of which as described above has no known human homologue) while normal controls do not have antibodies to PSP-1 or SP-1, and have only weak antibody response to CA6 (FIG. 5). The antibody response to CA6 was stronger in SD patients than in normal controls.

Each of the SD markers to which antibodies are determined according to the method of the invention are well characterized and are known in the art and their coding and amino acid sequences are available in GenBank. Each GenBank reference presented in this disclosure is incorporated herein by reference as of the date of this invention. It is expected that any mammalian CA6, PSP and SP-1 antigens (with the caveat that there is no know human homologue to SP-1) can be used with any of a wide variety of established immunoassays in the method of the invention to determine whether or not an individual produces antibodies directed to the antigens. In one embodiment, murine PSP is described by the sequences presented in GenBank entry NM_008953.2. In one embodiment, murine SP-1 described by the sequences presented in GenBank entry NM_009267.2. In one embodiment, CA6 is described by the sequences presented in GenBank entry NM_009802.2.

The protein antigens that are used for detecting autoantibodies according to the method of the invention can be made using techniques well known to those skilled in the art. For example, any DNA sequence encoding the antigens can be made using standard techniques and inserted into any number of expression vectors. Suitable expression vectors have been described in the literature and many are commercially available. Likewise, a wide variety of expression systems are known in the art and are commercially available, including prokaryotic and eukaryotic systems. The proteins can be isolated from the expression systems or any other suitable source and purified for use in the invention to any desired degree of purity.

The biological sample obtained from the individual can be any biological sample that comprises antibodies, and can comprise biological tissue and/or biological liquid. In various embodiments, the biological liquid is blood, serum or saliva.

The autoantibodies that are positively correlated with SD as described herein can be detected using any suitable technique, device, system and/or reagents, many of which are commercially available and/or are otherwise well know to those skilled in the art. In various, embodiments, suitable detection techniques include but are not necessarily limited to immunohistological techniques, Western blotting, multi-well assay plates adapted for detection of the antibodies, beads adapted for detection of the antibodies, a lateral flow device or strip that is adapted for detection of the antibodies, ELISA assays, or any modification of an ELISA assay that is suitable for detecting the antibodies. Further, any and alls isotypes of the antibodies can be detected. It is considered that the early antibodies are all or predominantly IgM and later antibodies are comprised of IgM and IgG. Thus, if desired, the invention can be adapted to discriminate between isotypes to assist in determining, for example, the stage of disease.

The method of the invention is suitable for performing on a biological sample obtained from an individual of any age or gender. The method may be performed once, or a series of tests may be performed to, for example, monitor an individual's response to a treatment.

In one embodiment, the invention is suitable for determining early SD. Early SD is considered to be a stage of SD before salivary and/or lachrymal gland function is diminished to a point where clinical symptoms of SD become manifest. Those skilled in the art will be able to recognize early SD, particularly when provided the benefit of the present disclosure. Further, the invention provides in some individuals, such as those with other autoimmune diseases or a family history SD, testing for SD before any symptoms appear.

In one embodiment, the invention comprises fixing the result of performing the method of the invention in a tangible medium of expression, such as a digitized computer record. The invention further comprises communication the result of the performing the method of the invention to a health care provider.

The invention also provides kits comprising the antigens to which the antibodies of SD patients are directed and may further comprise components for biological sample collection and reagents for antibody detection, positive controls, and the like. In one embodiment, the invention provides a kit comprising purified SP-1, PSP and CA6 proteins or fragments thereof that are recognized by antibodies produced by SD patients. Fragments of these proteins can be recognized by antibodies produced by individuals who have SD can be determined using routine skill if given the benefit of the present disclosure. In general, the fragments will be from 9 amino acids in length, up to one amino acid less than the full length the proteins, and including all integers from 9 amino acids up to one amino acid less than the full length of the proteins, inclusive. Each and every fragment of these proteins is therefore considered part of the instant disclosure for use in the present invention. Each of these fragments can be made and tested to determine whether antibodies from individuals who have SD recognize the fragments. The proteins or fragments thereof may be provided in isolated and purified form, and they may be associated with a solid matrix. The solid matrix may be present in as a component of any system that can be used for antibody detection, such as multi-well assay plates, beads, lateral flow devices or strips, or any other form or format that is suitable for keeping the proteins in a position whereby antibodies can bind to them and be detected in the method of the invention. The proteins may be covalently or non-covalently associated with the solid matrix.

The following Examples are intended to illustrate certain embodiments of the invention but are not meant to limit the invention.

EXAMPLE 1

This Example demonstrates the production of autoantibodies in the sera of SD mouse models in the early stages of SD.

In order to obtain the results presented in FIG. 1, sera were collected from IL-14aTG mice, NOD and C57BL/6 mice at 7 months of age. We expressed and purified SP-1, PSP and CA6 and used the purified proteins for Western blot analysis. Data shown are representative of 6 mice studied in each group. The left panel shows the serum of an IL-14aTG mouse that recognizes CA6 and PSP strongly and SP-1 weakly. The middle panel shows the same study with the serum of a C57BL/6 mouse. None of these auto-antigens were bound by C57BL/6 sera. The right panel shows the same study with the serum of an NOD mouse. Both CA6 and PSP are strongly recognized by this serum.

EXAMPLE 2

This Example demonstrates that LTA is found in the salivary gland secretions of IL-14aTG mice but not in littermate controls.

In order to obtain the data results presented in FIG. 2, salivary gland secretions were collected from IL-14a TG mice and various control mice at 12 months of age. Western blot assays were performed on the undiluted specimens. Lanes 1 and 2 are from IL-14a TG mice, lanes 3 and 4 from IL-14aTG. LTA−/− mice, lanes 5 and 6 from LTA−/− mice and lanes 7 and 8 from C57BL/6 mice. We also analyzed the histology of the submandibular and parotid glands in IL-14aTG.LTA−/− mice. These are normal.

EXAMPLE 3

This Example demonstrates that LTA is found in the sera of human SD patients. In order to obtain our results which are presented in FIG. 3, sera were obtained from 6 normal donors (age and sex matched to 6 of the Sjogren's disease patients) and 12 patients with Sjogren's disease. Lymphotoxin levels were determined by a commercially available ELISA (R&D SYSTEMS, Inc). The difference between the serum levels of lymphotoxin between normal controls and patients with Sjogren's disease was statistically significant (p=0.0011).

EXAMPLE 4

This Example demonstrates the identification of autoantibodies in the sera and salivary glands of IL-14aTG.LTA−/− mice. The data presented in FIG. 4 show that the serum of an IL-14aTG.LTA−/− mouse at 11 months of age reacts with SP-1, CA6 and PSP. The Western blot was performed as outlined in FIG. 1.

EXAMPLE 5

This Example demonstrates that serum obtain from human SD patients contains antibodies to murine CA6, murine PSP and murine SP-1. Western blots were performed essentially as described for FIG. 1, except sera were used from patients with SD or aged matched normal controls. Five patients and two normal controls were evaluated. Data shown are from one representative patient (all five patients showed similar results) and one normal control (both normal controls showed similar results). Patients with SD but not normal controls have antibodies to PSP and SP-1. The antibody response to CA6 was stronger in SD patients than in normal controls. Thus, we have demonstrated that the presence of antibodies to CA6, PSP and CA6 can be used to diagnose SD in humans.

While the invention has been shown and described with reference to certain preferred embodiments thereof, it will be understood by those skilled in the art that various changes in form and details may be made therein without departing from the spirit and scope of the invention as described.

We claim:

1. A method for determining whether an individual has Sjögren's disease (SD) comprising
   i) determining in a liquid biological sample from the individual the presence of antibodies directed to salivary gland protein 1 (SP-1), parotid secretory protein (PSP), carbonic anhydrase 6 (CA6), or determining a combination of the antibodies, and determining that the individual has SD based on the presence of the antibodies directed to the SP-1, or to the PSP, or to the CA6, or a combination of said antibodies, in amount that is greater than in a normal control; or
   determining in the biological sample obtained from the individual the absence of detection of antibodies to PSP and SP-1 and determining based on the absence of detection of the antibodies that the individual does not have SD.

2. The method of claim 1, wherein the combination of the antibodies includes antibodies to SP-1.

3. The method of claim 1, wherein the individual has early SD.

4. The method of claim 1, wherein the individual is a human.

5. The method of claim 4, wherein the determining of the antibodies is performed by ELISA assay.

6. The method of claim 5, wherein the antibodies in the biological sample that are directed to SP-1 bind to murine SP-1 in the ELISA assay.

7. The method of claim 1, wherein the individual who does not have SD has a lower amount of antibodies to CA6 than an individual who has SD.

8. The method of claim 1, further comprising determining the presence or absence of antibodies to lymphotoxin (LTA), mucin 10 (submandibular gland salivary mucin), salivary amylase 1, Ro, La, muscarinic receptor 3, fodrin, IL-14, interferon-α, and combinations thereof.

9. The method of claim 1, wherein the biological sample comprises blood, serum, or saliva.

* * * * *